United States Patent
Kim et al.

(10) Patent No.: US 8,247,638 B2
(45) Date of Patent: Aug. 21, 2012

(54) ABSORBENT ARTICLE SATURATION INDICATION SYSTEM AND METHOD

(75) Inventors: Jaeho Kim, Roswell, GA (US); John Gavin MacDonald, Decatur, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 656 days.

(21) Appl. No.: 12/336,631

(22) Filed: Dec. 17, 2008

(65) Prior Publication Data

US 2010/0152642 A1 Jun. 17, 2010

(51) Int. Cl.
*A61F 13/15* (2006.01)
*A61F 13/20* (2006.01)

(52) U.S. Cl. .............. 604/361; 604/385.17; 604/385.18

(58) Field of Classification Search ............. 604/11, 604/361, 385.17, 385.18; 73/73
See application file for complete search history.

(56) References Cited

U.S. PATENT DOCUMENTS

| | | | |
|---|---|---|---|
| 3,019,638 A * | 2/1962 | Klein | 73/73 |
| 3,139,854 A * | 7/1964 | Hedges et al. | 116/278 |
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,794,024 A * | 2/1974 | Kokx et al. | 604/361 |
| 3,802,817 A | 4/1974 | Matsuki et al. | |
| 3,849,241 A | 11/1974 | Butin et al. | |
| 4,340,563 A | 7/1982 | Appel et al. | |
| 4,357,938 A | 11/1982 | Ito et al. | |
| 4,488,928 A | 12/1984 | Ali Khan et al. | |
| 4,834,733 A | 5/1989 | Huntoon et al. | |
| 5,354,289 A * | 10/1994 | Mitchell et al. | 604/361 |
| 5,458,589 A | 10/1995 | Comin Dumong | |
| 5,599,338 A | 2/1997 | Enloe | |
| 5,769,813 A | 6/1998 | Peiler et al. | |
| 5,902,296 A * | 5/1999 | Fluyeras | 604/361 |
| 5,904,671 A * | 5/1999 | Navot et al. | 604/361 |
| 6,063,042 A * | 5/2000 | Navot et al. | 600/584 |
| 6,348,640 B1 | 2/2002 | Navot et al. | |
| 6,596,919 B2 | 7/2003 | Williams | |
| 7,214,848 B2 * | 5/2007 | DiSalvo et al. | 604/361 |
| 7,355,090 B2 * | 4/2008 | Ales et al. | 604/361 |
| 7,566,491 B2 * | 7/2009 | Dilnik et al. | 428/316.6 |
| 7,806,882 B1 * | 10/2010 | Larkin | 604/385.18 |
| 7,822,455 B2 * | 10/2010 | Hoss et al. | 600/347 |
| 7,826,879 B2 * | 11/2010 | Hoss et al. | 600/347 |
| 2003/0023214 A1 | 1/2003 | DiSalvo et al. | |
| 2004/0064114 A1* | 4/2004 | David et al. | 604/361 |
| 2007/0016156 A1* | 1/2007 | Burgdorf et al. | 604/385.18 |

FOREIGN PATENT DOCUMENTS

| | | |
|---|---|---|
| EP | 0 220 741 B1 | 2/1993 |
| EP | 1216673 A1 | 6/2002 |
| JP | 11-104178 A | 4/1999 |
| JP | 2003175076 * | 6/2003 |
| WO | WO 99/33428 A1 | 7/1999 |
| WO | WO 2008/035144 A1 | 3/2008 |

* cited by examiner

*Primary Examiner* — Tatyana Zalukaeva
*Assistant Examiner* — Susan Su
(74) *Attorney, Agent, or Firm* — Denise L. Stoker; Randall W. Fieldhack (57) ABSTRACT

An absorbent article includes an absorbent body in contact with a moisture activatable shrinking yarn in the form of a metering string. The metering string includes a hanging portion that is at least initially visible to a user when the absorbent article is in use. By observing the change in length of the hanging portion, a user wearing the absorbent article can determine how saturated the absorbent article has become. The metering string may be used with absorbent articles such as tampons and diapers.

19 Claims, 7 Drawing Sheets

ABSORBENT ARTICLE SATURATION INDICATION SYSTEM AND METHOD

The present invention relates generally to absorbent articles for absorbing menses or urine. More particularly, the present invention relates to absorbent articles in which a device is used to determine the saturation level of the article, the device being a moisture-activated shrinking yarn.

There are several types of absorbent articles on the market for absorbing menses and urine, and each article has only so much capacity to hold such fluids. There are times when it would be useful to know how saturated an article is, and whether it needs to be changed. This presents varying levels of difficulty depending on the article type.

For example, the only way to know how saturated a tampon has become is to remove it for visual inspection. The drawback of removal is that the tampon cannot be reinserted. Because the consequences of leaving a saturated tampon in the body outweighs the cost of throwing out partially used tampons, women can unnecessarily change tampons and spend more money per month on catamenial products than is needed.

In the case of a diaper product, one may need to inspect the diaper by removal to know how full the diaper is. This can be quite inconvenient, especially if the person wearing the diaper is elderly and infirm.

What is needed is a device that can indicate how saturated an absorbent article such as a tampon or diaper is without having to remove the tampon or diaper.

SUMMARY OF THE INVENTION

One aspect of the present invention is an absorbent article. The article includes an absorbent body having a first end and an opposite second end, and defining a length. A metering string is attached to the absorbent body, the metering string having an internal portion that maintains contact with the absorbent body, and a hanging portion that hangs freely from the absorbent body. The metering string is a moisture-activated shrinking material.

Another aspect of the present invention is a method of signaling the fullness of a tampon in a vagina. One step is the providing of a tampon having a withdrawl string and a metering string extending from a proximal end thereof, wherein the withdrawl string has a reference length. Another step is inserting the tampon into the vagina. Yet another step is comparing the metering string length to the reference length.

An additional aspect of the present invention is a tampon that includes a pledget having a circumference, a distal end for insertion and a proximal end opposite thereof. A withdrawl string having a reference length is attached to and extends from the proximal end of the pledget. The tampon also includes a metering string made with a moisture-activated shrinking yarn. The metering string has an internal portion and a hanging portion, wherein the internal portion is in contact with the pledget and extends from the distal end to the proximal end. The hanging portion extends from the proximal end of the pledget, adjacent the withdrawl string.

Various advantages of the present invention will become apparent to those skilled in the art in view of the following description and the accompanying drawings.

DESCRIPTION OF THE INVENTION

As used herein the term "nonwoven fabric or web" means a web having a structure of individual fibers or threads that are interlaid, but not in a regular or identifiable manner as in a knitted fabric. The term also includes individual filaments and strands, yarns or tows as well as foams and films that have been fibrillated, apertured, or otherwise treated to impart fabric-like properties. Nonwoven fabrics or webs have been formed from many processes such as for example, meltblowing processes, spunbonding processes, and bonded carded web processes.

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as, for example, described in U.S. Pat. Nos. 4,340,563; 3,692,618; 3,802,817; 3,338,992; 3,341,394; 3,502,763; 3,502,538; and 3,542,615. Spunbond fibers are quenched and generally not tacky when deposited onto a collecting surface. Spunbond fibers are generally continuous and have average diameters frequently larger than 7 microns, typically between about 10 and 20 microns.

As used herein the term "meltblown fibers" means fibers formed by extruding a molten thermoplastic material through a plurality of fine, usually circular, die capillaries as molten threads or filaments into converging high velocity, usually heated, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface often while still tacky to form a web of randomly disbursed meltblown fibers. Such a process is disclosed, for example, in U.S. Pat. No. 3,849,241.

Meltblown fibers are microfibers that may be continuous or discontinuous and are generally smaller than 10 microns in average diameter.

As used herein "bonded carded webs" or "BCW" refers to nonwoven webs formed by carding processes as are known to those skilled in the art and further described, for example, in U.S. Pat. No. 4,488,928 which is incorporated herein by reference. Briefly, carding processes involve starting with a blend of, for example, staple fibers with bonding fibers or other bonding components in a bulky ball that is combed or otherwise treated to provide a generally uniform basis weight. This web is heated or otherwise treated to activate the adhesive component resulting in an integrated, usually lofty nonwoven material.

As used herein, the term "hydrophobic" includes those materials that are not hydrophilic as defined. It will be recognized that hydrophobic materials may be treated internally or externally with treatments such as surfactants and the like to render them hydrophilic.

As used herein, the term "surface" and its plural generally refer herein to the outer or the topmost boundary of an object.

As used herein, the phrase "absorbent article" refers to devices which absorb and contain body fluids.

As used herein the "moisture-activated shrinking yarn" is a liquid-contractible material capable of shrinking upon contact with water. The yarn may be made from one or more filaments.

Generally, the present invention is an absorbent article that incorporates a moisture-activated shrinking yarn for measuring the saturation level of the absorbent body of the absorbent article. Absorbent articles of different forms have in common the absorbent body as described herein. The two particular types of absorbent articles discussed in detail herein include tampons and diapers. However, these examples are not meant to be limiting and it is contemplated that the present invention could be applied to any article that employs an absorbent body or other device for holding fluid.

Figure 1:
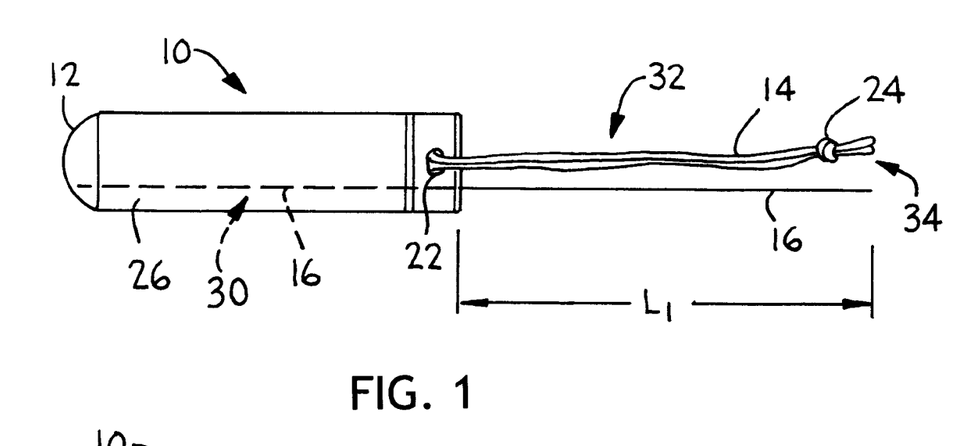
FIG. 1 is a side elevation of a tampon according to a first embodiment of the present invention, wherein the tampon is unused.

A tampon 10 is an absorbent member primarily designed to be worn by a woman during her menstrual period to absorb menses and other body fluid. Referring to FIG. 1, there is provided a tampon 10 having an absorbent pledget 12, a withdrawl string 14, and a metering string 16. The pledget 12 is normally compressed into the form of a cylinder and can have a blunt, rounded or shaped distal end 18. The distal end 18 is closest to the cervix when the tampon 10 is in use. The pledget 12 also has a proximal end 20 which is closest to the vaginal opening when the tampon 10 is in use.

As with any tampon, the distal end 18 is inserted into the body first, with the rest of the tampon following. Once inserted, the withdrawl string 14 and the metering string 16 hang freely from the vaginal opening. Insertion can be made digitally or by use of an applicator (not shown) as known in the art.

Catamenial tampons suitable for use in the present invention include an absorbent material formed into an absorbent body. The absorbent material can be formed from fibers that are assembled into an absorbent sheet or ribbon. Alternatively, the absorbent material can be formed from absorbent fibers that are assembled and compressed into a generally elongated and/or cylindrical configuration. The absorbent material is desirably formed from natural cellulosic fiber, such as cotton and rayon. For example, the absorbent material can be 100% cotton, 100% rayon, a blend of cotton and rayon fibers, or other materials known to be suitable for tampons, including artificial fibers such as polyester, polypropylene, nylon or blends thereof. The absorbent material may also include degradable fibers. Other types of materials or structures may also be used, such as cellulose sponge or a sponge formed from elastomeric materials. When formed, the absorbent material typically includes interstitial space or voids between the fibers or other materials.

Tampons 10 suitable for use in this invention are compressed into a unitary absorbent body of a size that may easily be inserted into the vaginal cavity. The absorbent material fiber orientation is typically in a linearly- or radially-wound structure. Tampons 10 are normally made in an elongated cylindrical form in order that they may have a sufficiently large body of material to provide the required absorbing capacity, but tampons 10 may be made in a variety of shapes. The tampon 10 compression may be achieved by predominantly longitudinally-, axially- or radially-applied pressure, or a combination thereof.

Commonly, a fluid permeable cover 11 is wrapped about the pledget 12 to avoid shredding of the pledget upon removal. The cover 11 is often made from a sheet of nonwoven fibers, e.g., a spunbond polypropylene sheet. The tampon 10 may also include one or more of various treatments to improve the performance of the tampon 10, including reduced friction and increased absorption, delivery of the therapeutic agent, or a combination of treatments.

The fibers from which the present absorbent products are made may be produced, for example, by the meltblowing or spunbonding processes, including those producing bicomponent, biconstituent, or polymer blend fibers that are well known in the art. The fibers produced in the spunbond and meltblown processes are microfibers as defined above.

The tampon 10 commonly has a withdrawal string 14 fastened to the proximal end 20 that serves as a means for withdrawing the tampon from the woman's vagina. The withdrawal string 14 can be looped through an aperture 22 formed transversely through the pledget 12. In addition, the withdrawal string 14 can have a knot 24 formed at the free end of the string to assure that the string 14 will not separate from the pledget 12.

The withdrawl string 14 is used not only for a length reference as described herein, but for removal of the tampon. The withdrawl string is made from a material that does not shrink or significantly expand when wetted. Also, it is desirable that the withdrawl string is hydrophobic and/or non-wicking. One example of a withdrawl string 14 is a monofilamentous polymers, Dacron, siliconized Dacron, coated cotton or the like.

In addition to the withdrawl string is the metering string 16. Metering string 16 is made from a material that shrinks upon wetting. Appropriate materials for the metering string 16 include yarns made from polyethylene glycol-based fibers, such as is available from Nitivy Company Ltd., Tokyo, Japan. These yarns are available in different degrees of shrinkage, from about 35% to about 60% of the original length after wetting. Other moisture-activated shrinking yarns include modified cellulose or rayon, for example; carboxymethylated cotton, methylated cotton, ethylated cotton, carboxymethylated polynosic rayon and the like.

Figure 1A:
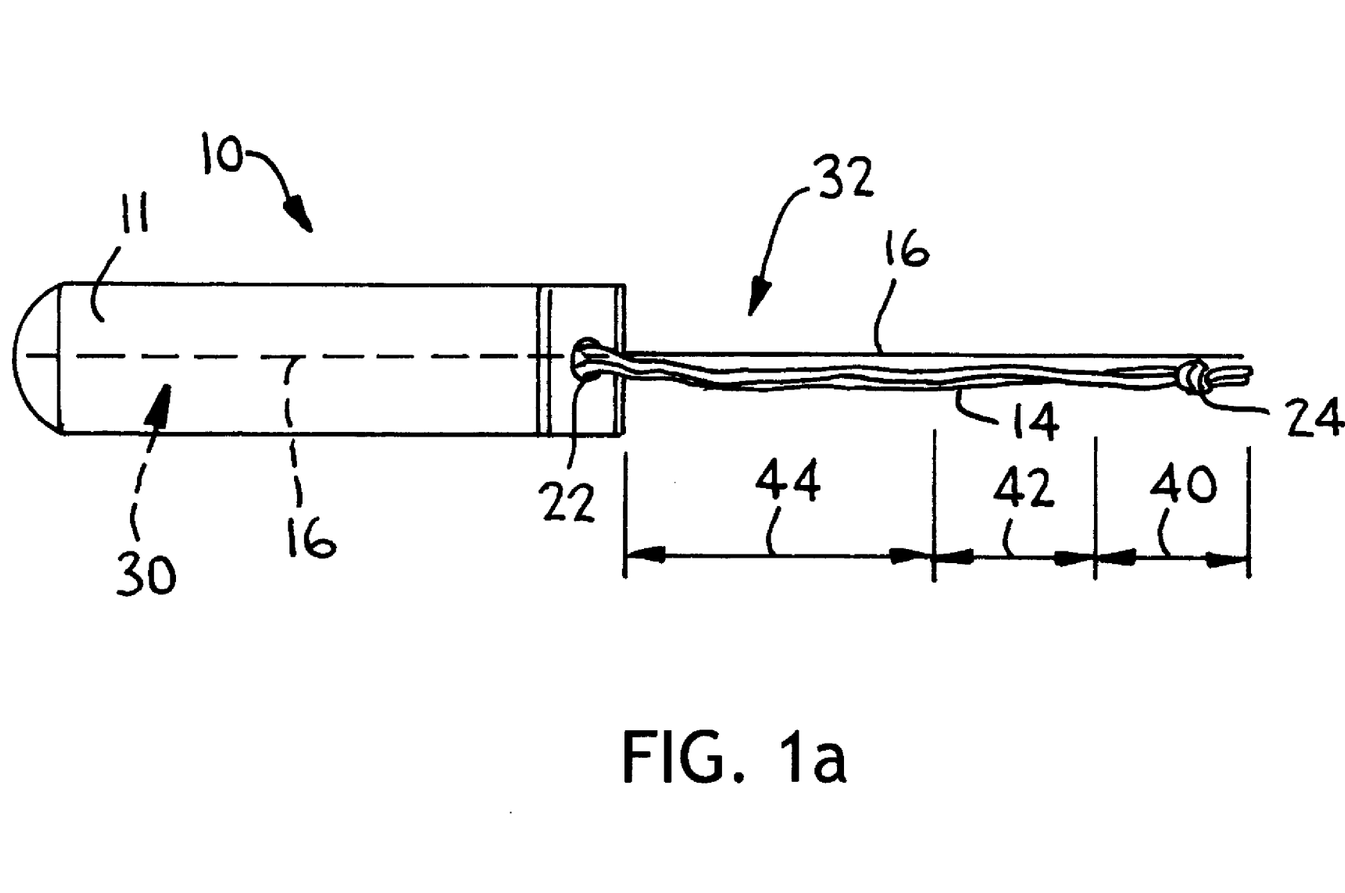
FIG. 1a is a side elevation of a tampon according to a second embodiment of the present invention, wherein the tampon is unused.
Figure 2:
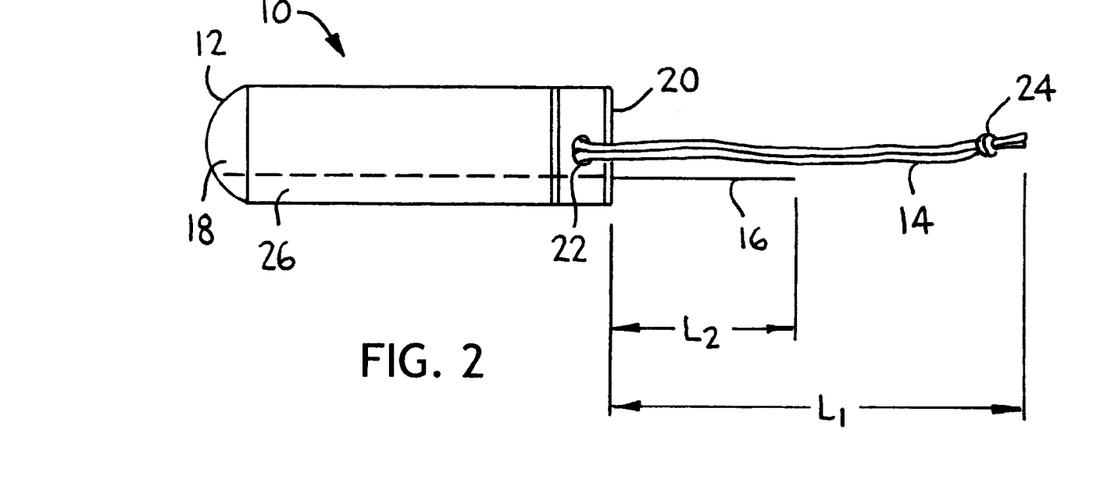
FIG. 2 is a side elevation of a tampon according to a first embodiment of the present invention, wherein the tampon is saturated.

Referring now to one embodiment of the present invention as shown in FIGS. 1 and 2, the metering string 16 is a continuous piece of string that is incorporated into the pledget 12 body. Desirably, the string 16 has an internal portion 30 that extends from the distal end 18 to the proximal end 20 of the pledget 12, and a hanging external portion 32 that extends from the proximal end 20 to the distal end 34 of the withdrawl string 14. Because of the central location of the withdrawl string 14 with respect to the pledget 12, the string 16 may be offset as shown. However, it is contemplated that the internal portion 30 of string 16 could substantially coincide with the longitudinal axis of the pledget 12 and extend from the distal end 18 to the aperture 22, with the external portion extending from aperture 22 to the distal end 34 of the withdrawl string (see FIG. 1*a*). The difference between a centrally located internal portion 32 versus an offset location is the speed at which the internal portion 32 makes contact with menses.

The internal portion 32 of string 16 may be attached to the pledget 12 at the distal end only. The attachment may be made with a water insoluble hot melt adhesive or the like. As little of the string 16 is adhered to the pledget 12 so as not to prohibit the pledget from expanding longitudinally.

Prior to use, the external portion 32 of string 16 may be substantially equal in length to the withdrawl string 14 (see FIG. 1). As the string 16 is exposed to menses, and as the pledget begins to expand longitudinally, the length of the external portion 32 goes from an initial length L1 to a shorter saturated length L2. The difference between lengths L1 and L2 may be used to gauge how saturated the tampon has become. For example, shrinkage of a predetermined distance can be used to signal that the tampon is full, and this information may be relayed to the user visually, tactilely or both.

In one embodiment, the withdrawl string 14 has colored zones so that visually, one can determine whether or not to remove the tampon. For example, as shown in FIG. 1*a*, the withdrawl string has three zones: a "green" zone 40, a "yellow" zone 42, and a "red" zone 44. The green zone 40 means that there has been very little menses penetration into the tampon, and it is safe to wear. The yellow zone 42 means that there is only a certain percentage of capacity left in which menses can be absorbed. In one embodiment, that percentage range of the yellow zone may be about 40-90 percent. In a further embodiment, the percentage range may be about 60-90 percent. The red zone may indicate that there is less than about 10-20 percent of the absorbent capacity left in the tampon, and it is time to change the tampon.

If a tactile warning is desired, then the user only needs to feel for the length difference between the withdrawl string 14 and the metering string 16. In one case, the starting length of the metering string may be equivalent to the withdrawl string as shown in FIG. 1. The user is informed of what length difference between the metering string 16 and the withdrawl string 14 will signal a tampon change. In another embodiment, the metering string 16 is initially longer than the withdrawl string. When the two strings become equal in length, it signals the user that it is time to change the tampon. In yet another embodiment the metering string 16 is shorter than the withdrawl string 14. When the withdrawl string 14 can no longer be felt outside the user's body, it signals the user that it is time to change the tampon.

In one particular example, a single filament of SL110 (lot k11KM) SOLVRON yarn (Nitivy Co. Ltd., Tokyo, Japan) metering string was cut into a 20 cm length and threaded through a KOTEX SECURITY tampon from the distal end 18 to the proximal end 20 along the longitudinal axis so that it coincided with the longitudinal axis of the pledget. The hanging portion 32 of the metering string was 15 cm long. Water was applied to the tampon by a syringe and the metering string shrinkage measured. The results are shown in Table 1:

TABLE 1

| Water Volume (ml) | Length Change of Hanging Portion (cm) |
|---|---|
| 1 | 0 |
| 2 | 0 |
| 4 | 2 |
| 10 | 6 |

Figure 3:
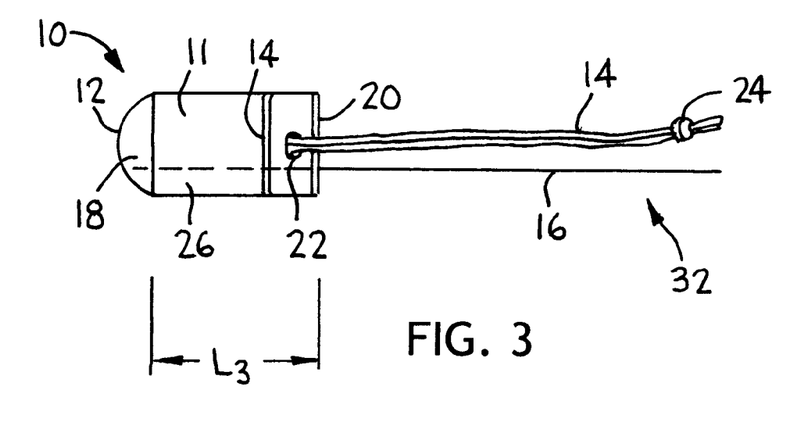
FIG. 3 is a side elevation of a tampon according to a second embodiment of the present invention, wherein the tampon is unused.
Figure 4:
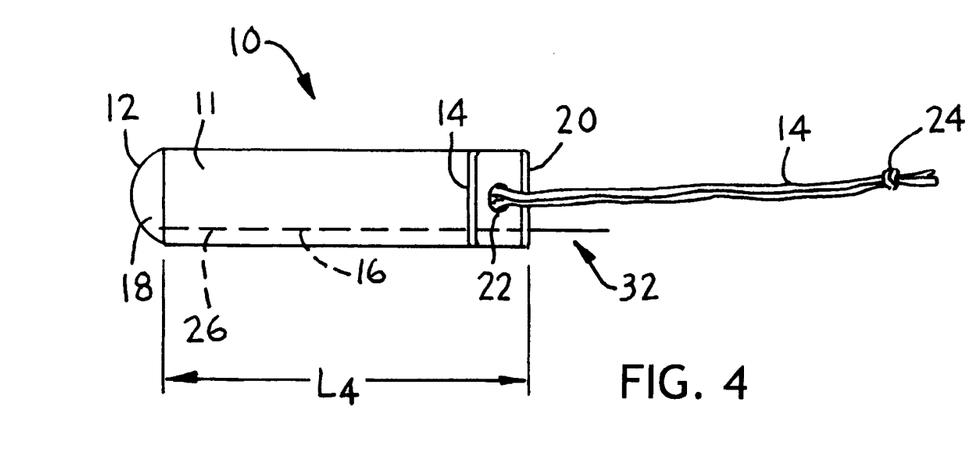
FIG. 4 is a side elevation of a tampon according to a second embodiment of the present invention, wherein the tampon is saturated.

In a second embodiment of the present invention as seen in FIGS. 3 and 4, the tampon 10 is significantly compressed in the longitudinal direction of the pledget 12. In this embodiment, not only does shrinkage of the metering string 16 occur, but the string in pulled significantly as the pledget 12 changes from an initial length L3 to a length L4, wherein L3<L4. Thus, the shrinking effect of metering string 16 is enhanced for easier detection of changes due to saturation levels of tampon 10. Other aspects of the invention remain the same as the previous embodiment.

Referring still to FIGS. 3 and 4, in one embodiment, length L3 is about 40-50 percent of the length L4. In another embodiment, length L3 is about 35-45 percent of the length L4. In yet another embodiment, length L3 is about 25-35 percent of the length L4.

Figure 5:
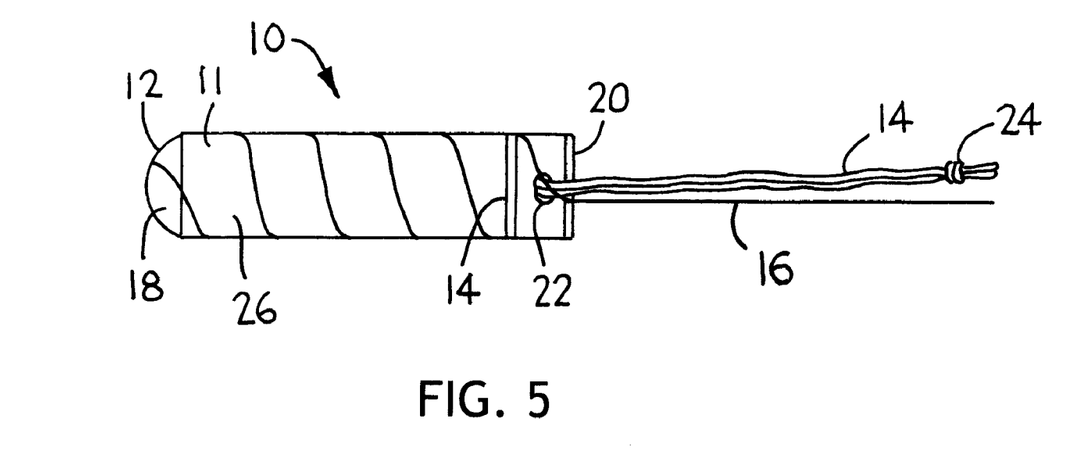
FIG. 5 is a side elevation of a tampon according to a third embodiment of the present invention, wherein the tampon is unused.
Figure 6:
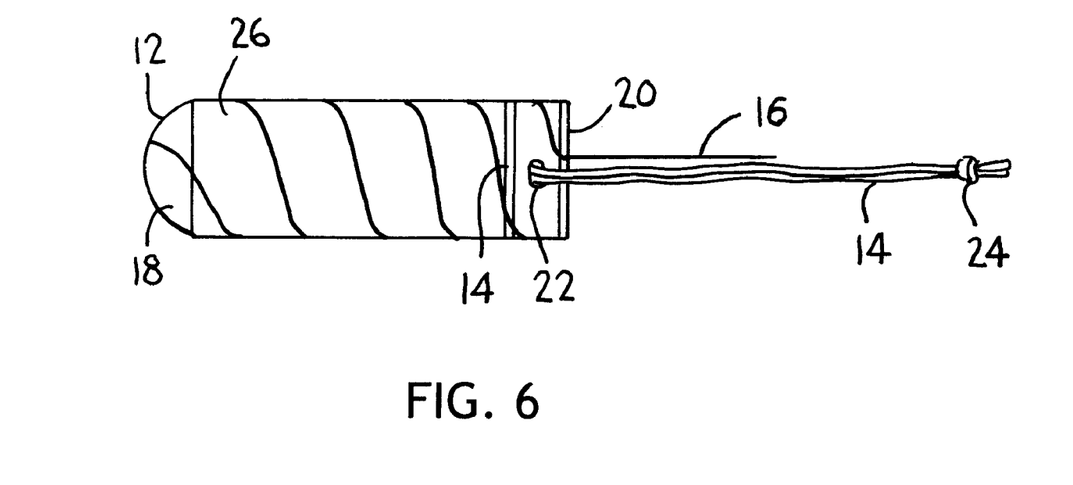
FIG. 6 is a side elevation of a tampon according to a third embodiment of the present invention, wherein the tampon is saturated.

In a further embodiment of the present invention as seen in FIGS. 5 and 6, the metering string 16 may be located on the outer surface of the pledget 12 either over or under the cover 11. Desirably, the metering string is adhered to the distal end 18 of pledget 12, and wound spirally about the pledget 12 to the proximal end 20. The remaining portion of string 16 hangs freely, extending along the length of withdrawl string 14.

Desirably, the wound portion does not overlap itself. The length of the wound portion may be two to five times the pledget circumference. In another embodiment, the length of the wound portion is longer than three times the pledget circumference.

Figure 9:
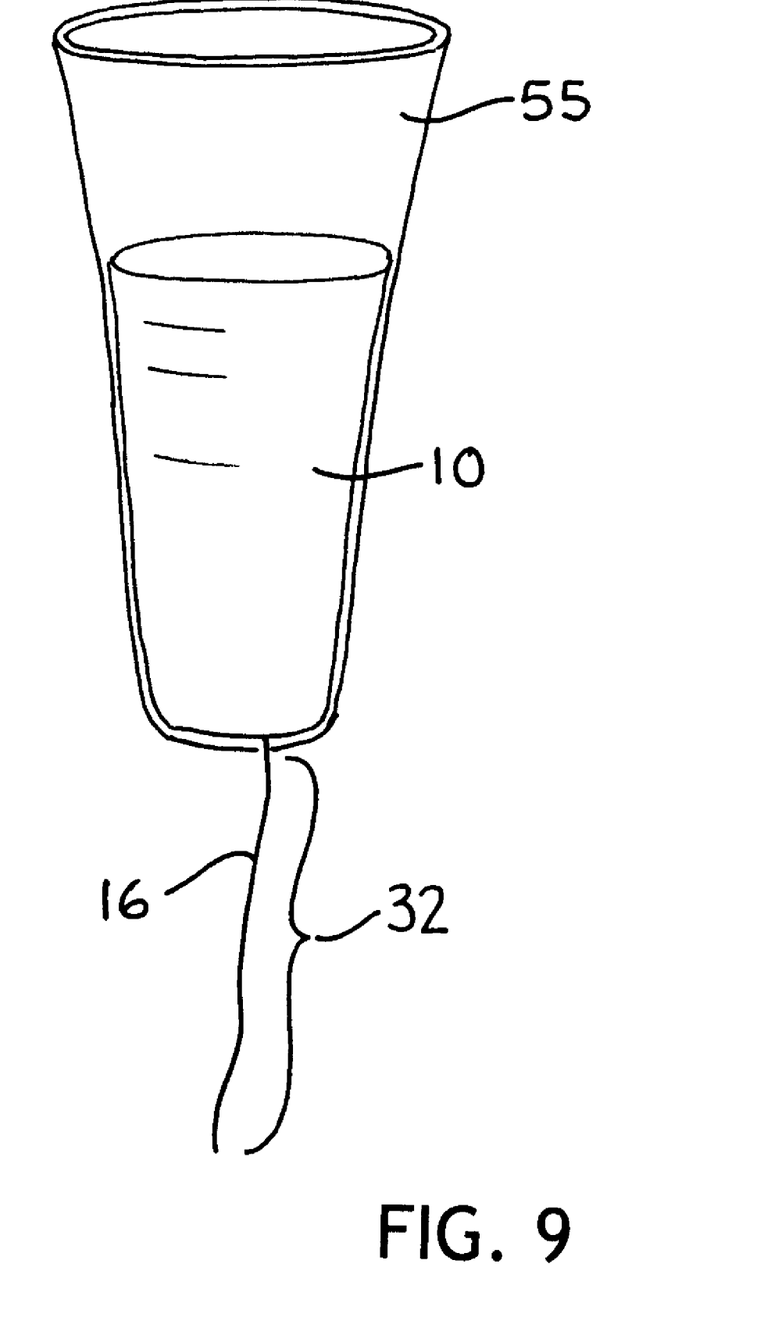
FIG. 9 is a front elevation of a tampon of the present invention in a testing device.

In one particular example, a single filament of SL110 (lot k11KM) SOLVRON yarn (Nitivy Co. Ltd., Tokyo, Japan) was cut into a 20 cm length and wound about the wrapper 11 of a tampon (KOTEX SECURITY tampon) five times. The hanging portion of the metering string was 12 cm in length. Referring to FIG. 9, the tampon was placed into a 50 ml conical tube (Becton Dickinson Company, Franklin Lakes, N.J.) with an aperture in the bottom for letting the hanging portion extend outwardly from the tube. Water was applied to the tampon and the hanging portion measured for shrinkage. The following Table 2 shows how the shrinkage occurred almost linearly with the water volume absorbed by the tampon:

TABLE 2

| Water Volume (ml) | Length Change of Hanging Portion (cm) |
|---|---|
| 1 | 1 |
| 2 | 2 |
| 4 | 4 |
| 10 | 6 |

Another type of absorbent article of the present invention will be described in terms of diapers worn about the lower torso. The absorbent articles of the present invention may be applicable to adult incontinent products, training pants, feminine care products and the like.

Figure 7:
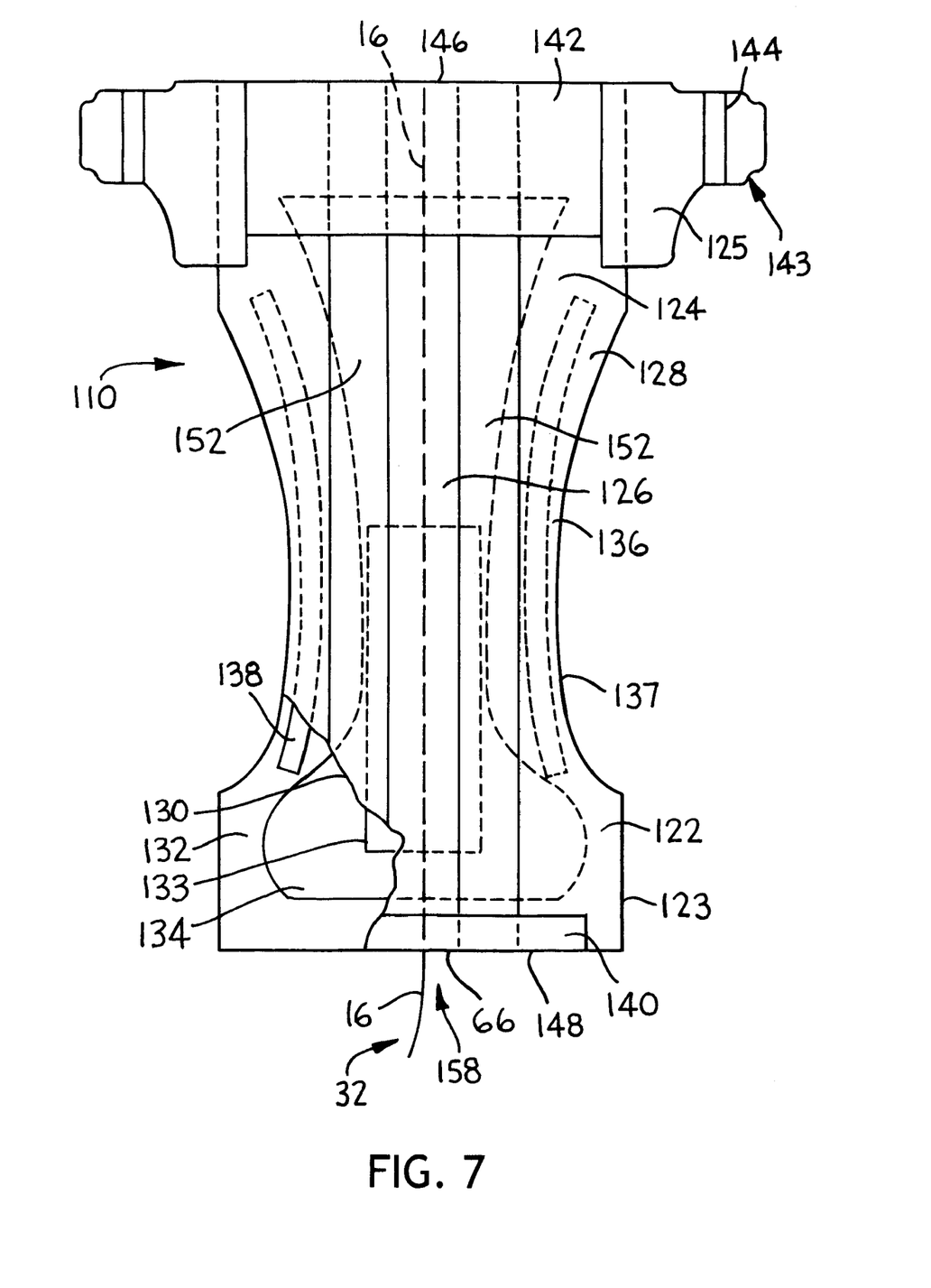
FIG. 7 is a plan view of a diaper according a fifth embodiment of the present invention.

FIG. 7 representatively illustrates a diaper 110 of the present invention in an unfastened condition. Portions of the diaper 110 are cut away to illustrate underlying structure. The surface of the diaper which contacts the wearer is facing the viewer in FIG. 7. The diaper 110 has a longitudinal direction 112 and a lateral direction 114. In the longitudinal direction 112, the diaper 110 defines a front portion 122, a back portion 124, and a crotch portion 126 connecting the front portion 122 and the back portion 124. The diaper 110 includes a bodyside liner 130, an outer cover 132 and an absorbent core 134 located between the bodyside liner 130 and the outer cover 132. The front portion 122 may include, at least partially, one or more front ears 123. The back portion 124 may include, at least partially, one or more back ears 125. The front ears 23 and/or the back ears 125 may be formed from extensions of the bodyside liner 130, the outer cover 132, combinations of both the bodyside liner 130 and the outer cover 132, or by the addition of one or more separate components as is known in the art.

The diaper 110 also includes a fastener system 143. The fastener system 143 includes one or more back fasteners 144 and one or more front fasteners 145 (see FIG. 8 for example). Portions of the fastener system 143 may be included in the front portion 122, the back portion 124, or both. The fastener system 143 is adapted to secure the diaper 110 about the waist of a wearer and maintain the diaper 110 in place during use.

The diaper 110 may also include a surge portion 133 joined to the absorbent core 134 and/or the bodyside liner 130. As used herein, reference to a front portion refers to that part of the diaper which is generally located on the front of a wearer when in use. Reference to the back portion refers to the portion of the diaper generally located at the back of the wearer when in use, and reference to the crotch portion refers to that portion which is generally located between the legs of the wearer when in use.

The crotch portion 126 has opposite longitudinal side portions 128 which may include a pair of elasticized, longitudinally-extending leg cuffs 136. The leg cuffs 136 are generally adapted to fit about the legs of a wearer in use and serve as a mechanical barrier to the lateral flow of body exudates. The leg cuffs 36 may be elasticized by a pair of leg elastics 138. The diaper 110 may further include a front waist elastic 140 and/or a back waist elastic 142.

The back portion 124 may have a straight back waist edge 146, an arcuate back waist edge 146, or a back waist edge 146 cut in other shapes as are known in the art. The front portion 122 may have a straight front waist edge 48, an arcuate front waist edge 148, or a front waist edge 148 cut in other shapes as are known in the art. As used herein, the term "straight" refers to edges that are substantially free from curves, bends, angles, notches or irregularities.

The diaper 110 may also include a pair of containment flaps 152 that may extend longitudinally along the diaper 110 and may also be adapted to provide a barrier to the flow of body exudates. It should be recognized that individual components of the diaper 110 may be optional depending upon the intended use of the diaper 110.

The bodyside liner 130 of the diaper 110, as representatively illustrated in FIG. 7, suitably presents a body facing surface which is intended to be worn adjacent the body of the wearer and is compliant, soft feeling and nonirritating to the wearer's skin. Further, the bodyside liner 130 may be less hydrophilic than the absorbent core 134 and may be sufficiently porous to be liquid permeable. A suitable bodyside liner 130 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers.

The bodyside liner 130 is suitably employed to help isolate the wearer's skin from fluids held in the composite absorbent core 134.

Figure 8:
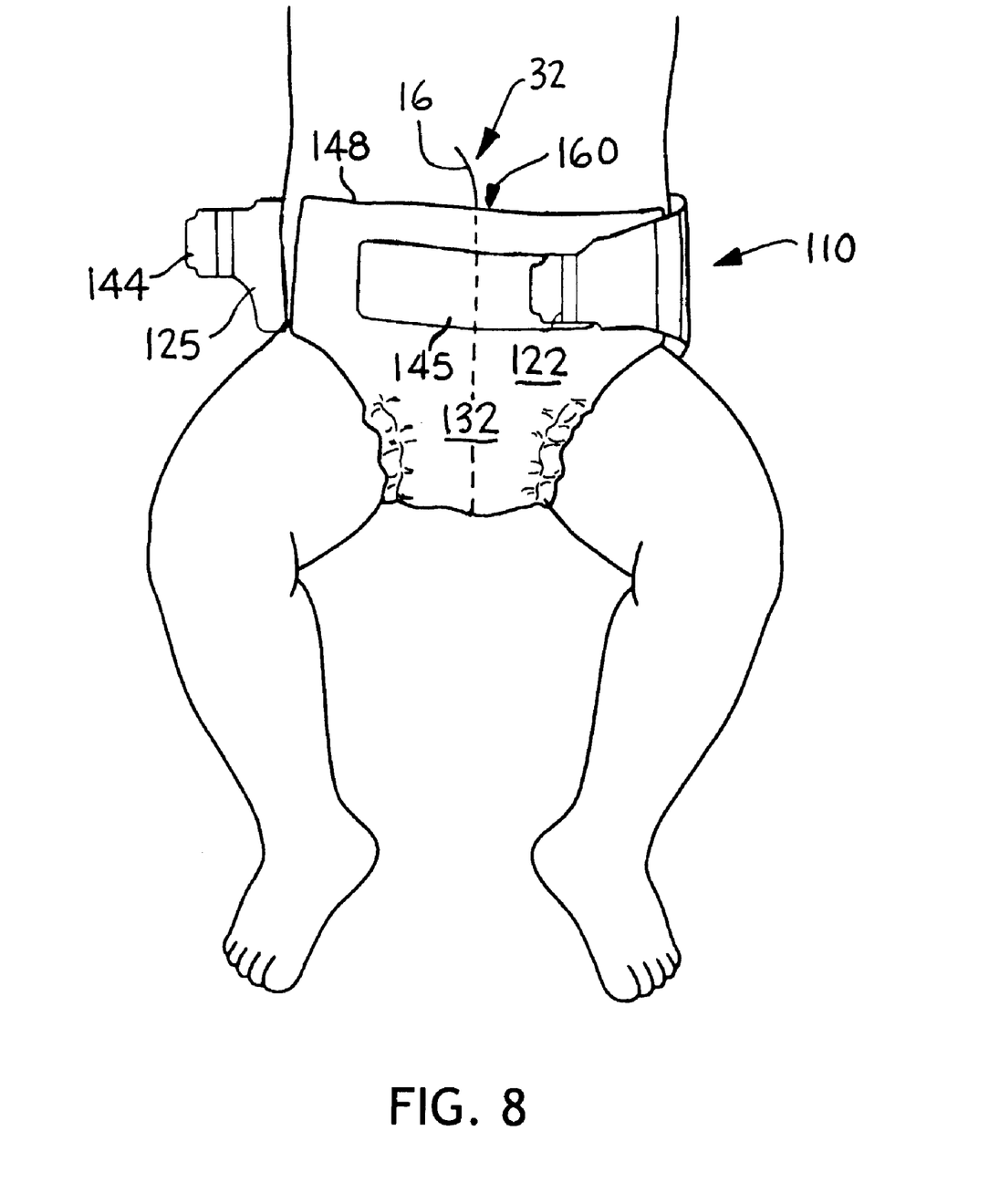
FIG. 8 is a front perspective view of the diaper of FIG. 7 shown on a child.

The outer cover 132 of the diaper 110, as representatively illustrated in FIG. 8, suitably presents a garment facing surface which is intended to be worn adjacent the clothing of the wearer. The outer cover 132 may be a polyethylene film. Alternative constructions of the outer cover 132 may comprise a woven or non-woven fibrous web layer which has been totally or partially constructed or treated to impart a desired level of liquid impermeability to selected regions of the backsheet that are adjacent or proximate the absorbent core 134. For example, a cloth-like backsheet may be composed of polypropylene spunbond fabric which is laminated and thermally bonded to a stretch-thinned polypropylene film. The outer cover 132 may optionally include a micro-porous, "breathable" material which permits vapors to escape from diaper 110 while still preventing liquid exudates from passing through. For example, the outer cover 132 may be composed of a microporous polymer film or a nonwoven fabric which has been coated or otherwise treated to impart a desired level of liquid impermeability. The outer cover 132 can also be embossed or otherwise provided with a matte finish to exhibit a more aesthetically pleasing appearance. The size of outer cover 132 is typically determined by the size of diaper 110 and the exact diaper design selected.

The bodyside liner 130 and outer cover 132 are generally joined in facing relationship with the absorbent core 134 located therebetween. The bodyside liner 130 and the outer cover 132 may be joined to each other around the outer periphery of the diaper 110 by any means known to those skilled in the art such as adhesive bonds, sonic bonds, thermal bonds, and the like, and combinations thereof. As used herein, the term "join", and derivatives thereof, encompass configurations wherein an element is directly secured to the other element by affixing the element directly to the other element, and configurations wherein the element is indirectly secured to the other element by affixing the element to intermediate member(s) which in turn are affixed to the other element.

The leg cuffs 136 are suitably formed by portions of the outer cover 132, and/or bodyside liner 130, which extend beyond the longitudinal sides of the absorbent core 134. Alternatively, the leg cuffs 136 can be formed from separate materials joined to the outer cover 132 and/or bodyside liner 130. In some embodiments, the leg cuffs 136 may have an arcuate shape resulting from a leg cut out 137. In other embodiments, the leg cuffs 136 may have a generally straight leg cut out 137.

The leg cuffs 136 may include leg elastics 138. Front waist elastics 140 and/or back waist elastic 142 may also be provided. The leg elastics 138 may be arranged to draw and hold the diaper 110 against the legs of the wearer. The waist elastics 140 and 142 may also be arranged to draw and hold the diaper 110 against the wearer, particularly at the waist. Materials suitable for use in forming leg elastics 38 and/or waist elastics 140 and 142 are known to those skilled in the art. Exemplary of such materials are strands or ribbons of a polymeric, elastomeric material which are adhered to the diaper 110 in a stretched position, or which are attached to the diaper while the diaper is pleated, such that elastic constrictive forces are imparted to the diaper 110. The leg elastics 138 and waist elastics 140 and 142 may have any configuration which provides the desired performance. The leg elastics 138 may be generally straight or optionally curved to more closely fit the contours of the legs and buttocks of the wearer and better contain bodily exudates. The leg elastics 138 and waist elastics 140 and 142 may be attached to the diaper 110 in any of several ways which are well known to those skilled in the art. For example, the elastics may be joined to the diaper 110 by ultrasonic bonding, thermal bonding, adhesive bonding, and the like, and combinations thereof.

In some embodiments, the one or more back fasteners 144 may be joined to the back portion 124, the back ears 125 or both and the one or more front fasteners 145 may be joined to the front portion 122, the front ears 123, or both. The one or more back fasteners 144 may be one or more discrete pieces of material joined to the diaper 110 and adapted to align with and work in conjunction with the one or more front fasteners 145, which may be one or more discrete pieces of material joined to the diaper 110. For example, the front fastener 145 may be a piece of loop material joined with the outercover 132 in the front portion 122 and configured to engage hook-type back fasteners 144 when the diaper 110 is wrapped about the waist and legs of a user.

Alternatively, the one or more front fasteners 145 may include portions of the outercover 132, the bodyside liner 130, or both and be configured to engage hook-type back fasteners 144. For example, the outercover 132 may be configured to be a non-woven material suitable for engagement with hook materials. In such an embodiment, hook-type fasteners 144 may be located at the back ear 25 and wrapped around the waist of the wearer. The hook-type fasteners 144 may then be engaged directly with the nonwoven outercover 132 to join the back portion 124 with the front portion 122 and secure the diaper 110 about the waist of the wearer.

Alternatively, the one or more front fasteners 145 may include hook-type fasteners and the one or more back fasteners 144 may include one or more complementary loop-type fasteners. In various embodiments, the one or more back fasteners 144 and the one or more front fasteners 145 may comprise any suitable materials adapted to join the back portion 124 to the front portion 122 of the diaper 110 thus securing the diaper about the waist of a wearer. Suitable fastening materials include hook and loop materials, adhesives, adhesive tapes, cohesives, snaps, buttons, latches, hooks, and the like, and combinations thereof. In some embodiments both the front portion 122 and the back portion 124 may include dual fasteners as is known in the art.

The absorbent core 134 is positioned between the bodyside liner 130 and the outer cover 132 to form the diaper 110. The absorbent core 134 is generally conformable and capable of absorbing and retaining body exudates. The absorbent core 134 may include superabsorbent material, staple fibers, binder fibers, and the like, and combinations thereof as is known in the art. The absorbent core 134 may have any of a number of shapes and sizes. For example, the composite absorbent core may be rectangular, I-shaped or T-shaped. The size and absorbent capacity of the absorbent core 134 should be compatible with the size of the intended wearer and the fluid loading imparted by the intended use of the diaper.

Containment flaps 152 may be connected to the bodyside liner or other components as is well known in the art. Suitable configurations of the containment flaps 152 are described, for example, in U.S. Pat. No. 5,599,338 issued Feb. 4, 1997, to K. Enloe, the entirety of which is incorporated herein by reference where not contradictory.

In one embodiment, a metering string 16 is disposed on top of the absorbent core 134, underneath the surge portion 133. The metering string 16 may extend from the back waist elastic 142 (where it is adhered thereto) to the front waist elastic. A hanging portion 32 extends from the front waist elastic. The metering string 16 is not adhered to the front waist elastic, the absorbent core 134, the surge portion 133, or the liner 130 so shrinkage can occur without gathering the diaper. Thus, the metering string 16 is able to slide freely along the diaper components (with the exception of the back waist elastic 142). The length of the hanging portion 32 is such that when the diaper is saturated, the metering string 16 is pulled into the interior of the diaper and no longer visible without removal of the diaper. Thus, the hanging portion 32 has a zero length when the diaper 110 is saturated. It is contemplated that the hanging portion 32 could extend from the back waist elastic 142 instead of the front waist elastic 140. In this case, metering string 110 would not be adhered to the back waist elastic 142, but would be adhered to the front waist elastic.

In another embodiment (not shown) the metering string is the same length or shorter than the absorbent core 134. In this case, the hanging portion 32 extends from either the front waist band 140 or the back waist band 142, and the other end of the metering string 16 terminated in the crotch portion 126.

As in the previous embodiment, the hanging portion 32 may have colored zones marked thereon. For example, at the outermost end of the hanging portion there may be a red zone, at a proximal end near the waist band there may be a green zone, with a yellow zone in between. When the metering string 16 shrinks and only the red zone is visible as a hanging portion, it signals that it is time for a diaper change.

The invention has been described with reference to various specific and illustrative embodiments and techniques. However, it should be understood that many variations and modifications may be made while remaining within the spirit and scope of the invention.

Accordingly, this invention is intended to embrace all such alternatives, modifications and variations that fall within the spirit and scope of the appended claims.

We claim:

1. An absorbent article comprising:
   an absorbent body having a first end and an opposite second end, and defining a length, wherein the absorbent body comprises a tampon pledget;
   a withdrawal string attached to the absorbent body; and
   a metering string attached to the absorbent body, the metering string comprising an internal portion that maintains contact with the absorbent body and a hanging portion that hangs freely from the absorbent body, wherein the metering string comprises a moisture-activated shrinking material, and wherein the metering and withdrawal strings are configured to provide an article saturation indication when compared.

2. The absorbent article of claim 1 wherein the metering string is greater in length than the absorbent body length and wherein the withdrawal string is attached to the second end.

3. The tampon according to claim 1, wherein the withdrawal string comprises a series of colored zones for visual reference.

4. The tampon according to claim 3, wherein the metering string comprises a series of colored zones for visual reference.

5. The tampon according to claim 1, wherein the metering string comprises a series of colored zones for visual reference.

6. The tampon according to claim 1, wherein the withdrawal string has a reference length, and wherein the hanging portion has a length substantially equal to the reference length.

7. A tampon comprising:
   a pledget having a circumference, a distal end for insertion and a proximal end opposite thereof;
   a withdrawal string having a reference length, the withdrawal string attached to and extending from the proximal end of the pledget; and a metering string comprised of a moisture-activated shrinking yarn, the metering string having an internal portion and a hanging portion, wherein the internal portion is in contact with the pledget and extends from the distal end to the proximal end, and the hanging portion extends from the proximal end of the pledget, adjacent the withdrawal string, and wherein the metering and withdrawal strings are configured to provide an article saturation indication when compared.

8. The tampon according to claim 7 wherein the withdrawal string comprises a series of colored zones for visual reference.

9. The tampon according to claim 8 wherein the metering string comprises a series of colored zones for visual reference.

10. The tampon according to claim 7 wherein the metering string comprises a series of colored zones for visual reference.

11. The tampon according to claim 7 wherein the hanging portion has a length substantially equal to the reference length.

12. The tampon according to claim 7 wherein the internal portion of the metering string is wound about the pledget to form a wound portion.

13. The tampon according to claim 12 wherein the wound portion extends from the distal end of the pledget to the proximal end.

14. The tampon according to claim 13 wherein the wound portion does not overlap itself.

15. The tampon according to claim 12 wherein the wound portion is has a length that is two to five times the pledget circumference.

16. The tampon according to claim 12 wherein the wound portion is longer than three times the pledget circumference.

17. The tampon according to claim 7 wherein the internal portion is embedded within the pledget.

18. The tampon according to claim 17 wherein the internal portion is disposed at a longitudinal axis of the pledget.

19. The tampon according to claim 7 wherein the metering string consists of a single filament.

* * * * *